(12) United States Patent
Wakisaka et al.

(10) Patent No.: US 7,488,499 B2
(45) Date of Patent: *Feb. 10, 2009

(54) HERBAL HAIR GROWTH INHIBITOR AND DEPILATION ACCELERATOR

(75) Inventors: Etsuji Wakisaka, Haga-gun (JP); Takashi Kitahara, Haga-gun (JP); Naoko Tsuji, Haga-gun (JP); Hiroshi Kusuoku, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/246,466

(22) Filed: Sep. 19, 2002

(65) Prior Publication Data

US 2003/0077241 A1 Apr. 24, 2003

(30) Foreign Application Priority Data

Sep. 20, 2001 (JP) ............................. 2001-286422
Sep. 20, 2001 (JP) ............................. 2001-286423

(51) Int. Cl.
*A61K 36/00* (2006.01)

(52) U.S. Cl. .................................................... 424/725

(58) Field of Classification Search .............. 424/195.1, 424/725, 400, 401, 773, 774, 775, 776, 777, 424/778, 779; 514/783
See application file for complete search history.

(56) References Cited

U.S. PATENT DOCUMENTS 6,171,595 B1   1/2001   Suzuki et al.
6,375,948 B1   4/2002   Tsuji et al.

FOREIGN PATENT DOCUMENTS

| CN | 1137929 A   | * | 12/1996 |
| EP | 0 296 625   |   | 12/1988 |
| JP | 355049305 A | * | 4/1980  |
| JP | 59101413 A  | * | 6/1984  |
| JP | 60-146829   | * | 8/1985  |
| JP | 04-243834   | * | 8/1992  |
| JP | 04-342535   | * | 11/1992 |
| JP | 05310537 A  | * | 11/1993 |
| JP | 2000-264814 | * | 9/2000  |
| JP | 20010644151 | * | 3/2001  |

OTHER PUBLICATIONS

Phillipson, J. New Drugs From Nature—It Could Be Yew; Phytotherapy Research 13 (1999) pp. 2-8.*
Revilla et al. Comparison of Several Procedures Used for The Extraction of Anthocynains From Red Grapes; J. Agric. Food Chem. 1998, 46, pp. 4592-4597.*

* cited by examiner

*Primary Examiner*—Patricia Leith
(74) *Attorney, Agent, or Firm*—Oblon, Spivack, McClelland, Maier & Neustadt, P.C.

(57) ABSTRACT

The present invention relates to a hair growth inhibitor and a depilation accelerator, each comprising a crude drug selected from *Bupleuri Radix, Perillae Herba, Rhel Rhizoma* and *Akebiae Caulis*, or an extract thereof. This inhibitor or accelerator makes it possible to inhibit the growth of body hair or promote depilation, respectively, thereby reducing the frequency of hair removal treatment. Moreover, it makes the hair body finer, thereby facilitating the removal of the hair from feet or arms.

9 Claims, No Drawings

HERBAL HAIR GROWTH INHIBITOR AND DEPILATION ACCELERATOR

TECHNICAL FIELD

The present invention relates to a hair growth inhibitor for retarding hair growth at arms or feet; and also a depilation accelerator.

BACKGROUND ART

The body hair of mammals serves to biologically protect important organs such as head, chest, arms and feet. In recent years, however, the body hair, particularly, that of arms and feet tends to be regarded undesirable from the aesthetic viewpoint. To meet such a tendency, a variety of body hair removing methods, such as mechanical removing method using a shaver, hair-tweezers or the like and, a method of rooting up the hair by using a depilatory and a method making use of the chemical action of a hair removing agent.

These hair removing methods however give a physical or chemical stimulus to the skin and are usually accompanied with a pain or discomfort. Although there is a little difference in durability among the methods, their effects do not last permanently, which requires further hair removal treatment after the passage of a predetermined time. There is accordingly a demand for reducing the frequency of the hair removal treatment.

An object of the present invention is therefore to provide a hair growth inhibitor and a depilation accelerator capable of suppressing hair growth and accelerating depilation, respectively, thereby reducing the frequency of the body hair removal treatment.

DISCLOSURE OF THE INVENTION

The present inventors have searched for highly safe natural substances. As a result, they have found that specific plants have excellent hair growth retarding action and depilation accelerating action.

In one aspect of the present invention, there is thus provided a hair growth inhibitor and a depilation accelerator, each comprising a crude drug selected from *Bupleuri radix, Perillae herba, Rhei rhizoma* and *Akebiae caulis*, or an extract thereof.

In another aspect of the present invention, there is also provided the use, for the preparation of a hair growth inhibitor or a depilation accelerator, of a crude drug selected from *Bupleuri radix, Perillae herba, Rhei rhizoma* and *Akebiae caulis*, or an extract thereof.

In a further aspect of the present invention, there is also provided a method for removing the body hair, which comprises applying, to the skin, a crude drug selected from *Bupleuri radix, Perillae herba, Rhei rhizoma* and *Akebiae Caulis*, or an extract thereof.

BEST MODES FOR CARRYING OUT THE INVENTION

The crude drugs to be contained in the hair growth inhibitor or depilation accelerator of the present invention are plant crude drugs. The "*Bupleuri radix*" is the root of *Bupleurum falcatum* L. belonging to the family of Umbelliferae or a variant thereof; "*Perillae herba*" is the greenery of *Perilla frutescens* Britton var. *acuta* Kudo or an allied species thereof belonging to the family of "Labiatae"; "*Rhei rhizoma*" is the tuber of *Rheum palmatum* L., *Rheum tanguticum* Maximowicz, *Rheum officinale* Baillon, or *Rheum coreanum* Nakai or a hybride therebetween belonging to the family of Polygonaceae; and "*Akebiae caulis*" is the volubile stem (usually, horizontally-cut one) of *Akebia quinata* Decaisne belonging to the family of Lardizabalaceae or a congener thereof. The above-described crude drugs have already been used as a drug or a raw material therefor, but they are utterly unknown to have hair growth suppressing action and depilation accelerating action.

The term "an extract thereof" as used herein means a solvent extract available by extracting the above-described crude drug at normal temperature or under heating or through an extracting device such as Soxhlet extractor, or its dilute solution, concentrate or dry powder. The extract may be a mixture of at least two of the above-described crude drugs.

Examples of the solvent used for extraction include water, alcohols such as methanol, ethanol, propanol and butanol, polyhydric alcohols such as polypropylene glycol and butylene glycol, ketones such as acetone and methyl ethyl ketone, esters such as methyl acetate and ethyl acetate, linear or cyclic ethers such as tetrahydrofuran and diethyl ether, halogenated hydrocarbons such as dichloromethane, chloroform and carbon tetrachloride, hydrocarbons such as hexane, cyclohexane and petroleum ether, aromatic hydrocarbons such as benzene and toluene, polyethers such as polyethylene glycol, pyridines, and supercritical carbon dioxide. They may be used either singly or in combination.

From the above-described extract, inactive impurities can be removed by a technique such as liquid-liquid partition. Use of such a purified extract is preferred in the present invention. If necessary, the extract may be used after deodorization or decoloring in a known manner.

The above-described crude drug or extract thereof can be used as is as the hair growth inhibitor or depilation accelerator of the present invention. It can also be used after dilution, or in the powder or paste form after concentration or lyophilization.

The crude drug or extract thereof thus prepared exhibits excellent hair growth suppressing action as shown later in Examples and has high safety so that a hair growth inhibitor available from the crude drug or extract thereof is usable as cosmetic, drug or quasi drug.

It is preferred to formulate the hair growth inhibitor or depilation accelerator of the present invention as a dermatologic preparation for external use, particularly, a hair-removing, depilatory or shaving cosmetic composition. Specific examples include hair removers in the form of a paste, cream or aerosol, depilatories in the form of a wax, gel or sheet, agents in the form of a lotion or cream used for treatment after hair removal or depilation, antiperspirant and deodorant cosmetic compositions such as deodorant lotion, deodorant powder, deodorant spray or deodorant stick, pre-shaving agents such as pre-shaving lotion, shaving agents such as shaving cream, and after-shaving agents such as after-shaving lotion.

In the hair growth inhibitor or depilation accelerator of the present invention, the particularly preferred content of the crude drug permitting the exhibition of hair growth suppressing effect or depilation accelerating effect is 0.01 to 10 wt. %.

In the hair growth inhibitor or depilation accelerator of the present invention, various components usually employed for the formulation are incorporated. Examples include, as well as oil components usually employed as components of a cosmetic composition, surfactants, purified water, alcohols, chelating agents, pH regulators, antiseptics, thickeners, emulsifiers, emulsion stabilizers, colorants, and perfumes, ultraviolet absorbers, skin whitening cosmetics, wrinkle soothing agents, humectants, regulators of sebum excretion, softeners, keratin protectives, drug efficacy ingredients, antioxidants and solvents. By mixing these components as needed, cosmetics, drugs for external application and quasi drugs can be formulated.

To the hair growth inhibitor or depilation accelerator of the present invention, a keratolytic agent or a component having hair-growth controlling or depilatory action such as thioglycolic acid or a salt thereof can also be added as needed. Examples of the keratolytic agent include lactic acid, bioprase, salicylic acid, glycolic acid, citric acid and malic acid. Examples of the salt of thioglycolic acid include not only sodium salt, potassium salt and ammonium salt but also alkanolamine salts such as monoethanolamine, diethanolamine and triethanolamine. Each of these keratolytic agents, or thioglycolic acid or salts thereof is preferably added in an amount of 0.01 to 10 wt. %, particularly 0.05 to 5%.

EXAMPLES

Preparation Example 1

Preparation of Crude Drug Extract

In a manner known per se in the art, 100 ml of each extract shown in Table 1 was prepared.

TABLE 1

| Crude drug | Site to be extracted | Extracting solvent |
|---|---|---|
| Bupleuri radix | Root | 50% aq. ethanol soln. |
| Perillae herba | Leaf | 50% aq. ethanol soln. |
| Rhei rhizoma | Tube | 50% aq. ethanol soln. |
| Akebiae caulis | Stem | 50% aq. ethanol soln. |

Example 1

Hair Growth Inhibition Test Using Mice

The back of each of 6-week-old C3H mice (one group consisting of 5 mice) was shaved by 2×4 cm$^2$ by electric clippers and treated with depilatory cream so as not to injure its skin. From the next day, the test substance was applied by 20 μL/once/day to the shaved portion for 3 weeks. The test substance was dissolved in a solvent (50% ethanol) to give a concentration as shown in Table 2. Only the solvent was applied to a control group. Two weeks later, in order to observe hair regrowth, the picture of the shaved portion was taken at a fixed magnification. The area ratio of the regrowth hair (regrowth hair area/shaved area) was measured by an image analyzer and compared with that of the control group. The hair growth ratio is expressed as % relative to the area ratio of the regrowth hair of the control group set at 100. The results are shown in Table 2.

TABLE 2

| Test substance | Concentration of the solution | Hair growth ratio 2 weeks after shaving |
|---|---|---|
| 50% Ethanol | | 100% |
| Bupleuri radix | 0.01% | 60% |
| Perillae herba | 0.01% | 81% |
| Rhei rhizoma | 0.01% | 90% |
| Akebiae caulis | 0.01% | 15% |

From Table 2, it has been found that the crude drugs of the present invention each exhibited excellent hair growth inhibitory effect.

Example 2

Evaluation Test on Depilation Resistance on the Back of Mice (1) Preparation of Test substance The extract of each of the crude drugs shown in Table 1 was dissolved or suspended in a solvent (50% ethanol) to give a dry solid concentration shown in the table, whereby the corresponding test substance was prepared.

(2) Test Method

The back of each of 49-day-old C3H/HeNCrj mice (one group consisting of 20 mice) was shaved by 2×4 cm$^2$ by electric clippers and treated with depilatory cream so as not to injure its skin. Application of each of the test substances by 100 μL /twice/day to the shaved site was started one week before shaving and it was continued for 6 weeks, while only the solvent was applied to a control group. After 8 weeks, the mice were sacrificed. A CELLO TAPE, (trade mark, product of NICHIBAN Co., Ltd.; 2.5 cm wide) was adhered to the back. It was then peeled off by a predetermined force from the tail portion. By a punch of 8 mm in diameter, four pieces were punched out from the resulting tape. In accordance with Equation A, the weight of depilated hair was calculated from the weight of the four pieces punched out from the tape. In Equation B, a weight ratio of the depilated hair was determined with that of the control group as 100%. The results are shown in Table 3.

Equation A:

$$\text{Weight of depilated hair} = (\text{Weight of the tape to which hair has been adhered} - \text{Weight of the tape})$$

Equation B:

$$\text{Weight ratio of depilated hair (\%)} = \frac{\text{Weight of depilated hair at the site to which the test substance has been applied}}{\text{Average weight of depilated hair at the site to which the solvent has been applied}} \times 100$$

TABLE 3

| Test substance | A weight ratio of depilated hair (%) |
|---|---|
| Control (application of solvent) | 100 |
| Bupleuri radix (0.01%) | 106 |
| Perillae herba (0.01%) | 123 |
| Rhei rhizoma (0.01%) | 124 |
| Akebiae caulis (0.01%) | 136 |

From Table 3, it has been observed that the group to which the crude drug extract has been applied shows a significant concentration-dependent increase in the weight of the depilated hair per predetermined area of the tape. It suggests that the crude drug extract has depilation accelerating effect.

INDUSTRIAL APPLICABILITY

Use of the hair growth inhibitor or depilation accelerator of the present invention makes it possible to suppress the growth of the body hair or promote the depilation of the body hair, thereby reducing the frequency of the hair removal treatment. Moreover, it makes the body hair finer, which facilitates the removal of the body hair from the feet or arms.

What is claimed is:

1. A method for accelerating depilation, which comprises:
    applying to the skin and hair, a depilation accelerating effective amount of a composition comprising an aqueous alcohol solution extract of *Perillae herba* to accelerate depilation of said hair to which said composition has been applied; and
    depilating said hair to which said composition has been applied.

2. The method of claim 1, wherein said extract of *Perillae herba*, is present in said composition in an amount of from 0.01 to 10 wt %.

3. The method of claim 1, wherein the skin and hair to which the composition is applied are in an area selected from the group consisting of the body, arms and feet.

4. A method for accelerating depilation, which comprises:
    applying to the skin and hair, a depilation accelerating effective amount of a composition comprising one of an aqueous alcohol solution extract of *Perillae herba*, a crude drug, or an extract of said crude drug; and at least one member selected from a keratolytic agent, thioglycolic acid and a salt of thioglycolic acid, to accelerate depilation of said hair to which said composition has been applied; and depilating said hair to which said composition has been applied; wherein said crude drug is *Akebiae caulis*.

5. The method of claim 4, wherein said composition comprises said crude drug of *Akebiae caulis* or extract thereof.

6. The method of claim 5, wherein said crude drug or extract thereof is present in said composition in an amount of from 0.01 to 10 wt %.

7. The method of claim 5, wherein the skin and hair to which the composition is applied are in an area selected from the group consisting of the body, arms and feet.

8. The method of claim 4, wherein said extract of *Perillae herba*, is present in said composition in an amount of from 0.01 to 10 wt %.

9. The method of claim 4, wherein the skin and hair to which the composition is applied are in an area selected from the group consisting of the body, arms and feet.

* * * * *